US00PP30496P3

(12) United States Plant Patent
MacGregor et al.

(10) Patent No.: US PP30,496 P3
(45) Date of Patent: May 14, 2019

(54) ***ANEMONE* PLANT NAMED 'MACANE017'**

(50) Latin Name: ***Anemone* L.**
Varietal Denomination: Macane017

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 0 days.

(21) Appl. No.: 15/731,873

(22) Filed: Aug. 17, 2017

(65) Prior Publication Data

US 2018/0242494 P1 Aug. 23, 2018

(30) Foreign Application Priority Data

Feb. 7, 2017 (QZ) ..... PBR 2017/0335

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
See application file for complete search history.

(56) References Cited

PUBLICATIONS

UPOV Pluto Plant Variety Database, retrieved from https://www3.wipo.int/pluto/user/en/index.jsp, application date Apr. 15, 2017.*

* cited by examiner

*Primary Examiner* — Keith O. Robinson
(74) *Attorney, Agent, or Firm* — Samuel R. McCoy, Jr.

(57) ABSTRACT

'Macane017' is a new and distinctive variety of *Anemone* hybrid which is characterized by a compact growth habit, white flowers with alternate petals colored dark violet-blue on the lower surface, single flowers, and a long flowering season. The new variety propagates successfully by stem cuttings and tissue culture and has shown to be uniform and stable in the resulting generations from asexual propagation.

4 Drawing Sheets

Latin name of the genus and species: The Latin name of the genus and species of the novel variety disclosed herein is *Anemone* L.

Variety denomination: The inventive variety of *Anemone* disclosed herein has been given the variety denomination 'Macane017'.

CROSS REFERENCE TO RELATED APPLICATIONS

This application claims priority to the Community Plant Variety Rights application number 2017/0335, filed Feb. 7, 2017, which is herein incorporated by reference.

BACKGROUND OF THE INVENTION

Parentage: 'Macane017' is the result of a controlled cross-pollination breeding program carried out by the inventors at their commercial nursery in Kirkcudbright, Scotland, in 2007. The inventors began by performing a controlled cross-pollination of *Anemone rupicola* (unnamed and unpatented), the seed parent, with *Anemone hupehensis* var. japonica 'Pamina' (unpatented), the pollen parent. An F1 seedling from said cross was grown to maturity and then pollinated with an unnamed *Anemone hupehensis* seedling with a dwarf growth habit and a pink double flower, developed by the inventors (unpatented). Said pollination was performed in an insect proof environment. Seed from said cross was harvested, then germinated, and the resulting seedlings were then grown to a mature size in a protected poly tunnel greenhouse. In 2008, the inventors selected the new *Anemone* cultivar due to its unique flower and bloom characteristics. This new and distinctive cultivar was given the name 'Macane017'.

Asexual Reproduction: Asexual reproduction of 'Macane017' was first accomplished in 2008 by way of root cuttings at the inventor's nursery in Kirkcudbright, Scotland. After several years of experimentation, 'Macane017' was also asexually reproduced by way of meristematic tissue culture micro propagation at a plant tissue culture laboratory in the Netherlands. Successive generations produced from both root cuttings and tissue culture have shown that the unique features of the instant cultivar are stable and reproduce true to type.

SUMMARY OF THE INVENTION

The cultivar 'Macane017' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anemone* cultivar, 'Macane017'. These traits, in combination, distinguish 'Macane017' as a new and distinct cultivar.

1. *Anemone* 'Macane017' exhibits a compact growth habit; and

2. *Anemone* 'Macane017' exhibits white flowers with alternate petals colored dark violet-blue on the lower surface; and
3. *Anemone* 'Macane017' exhibits single flowers; and
4. *Anemone* 'Macane017' exhibits a long flowering season, from summer through autumn when grown in Kirkcudbright, Scotland.

BOTANICAL DESCRIPTION OF THE PLANT

Figure 1:
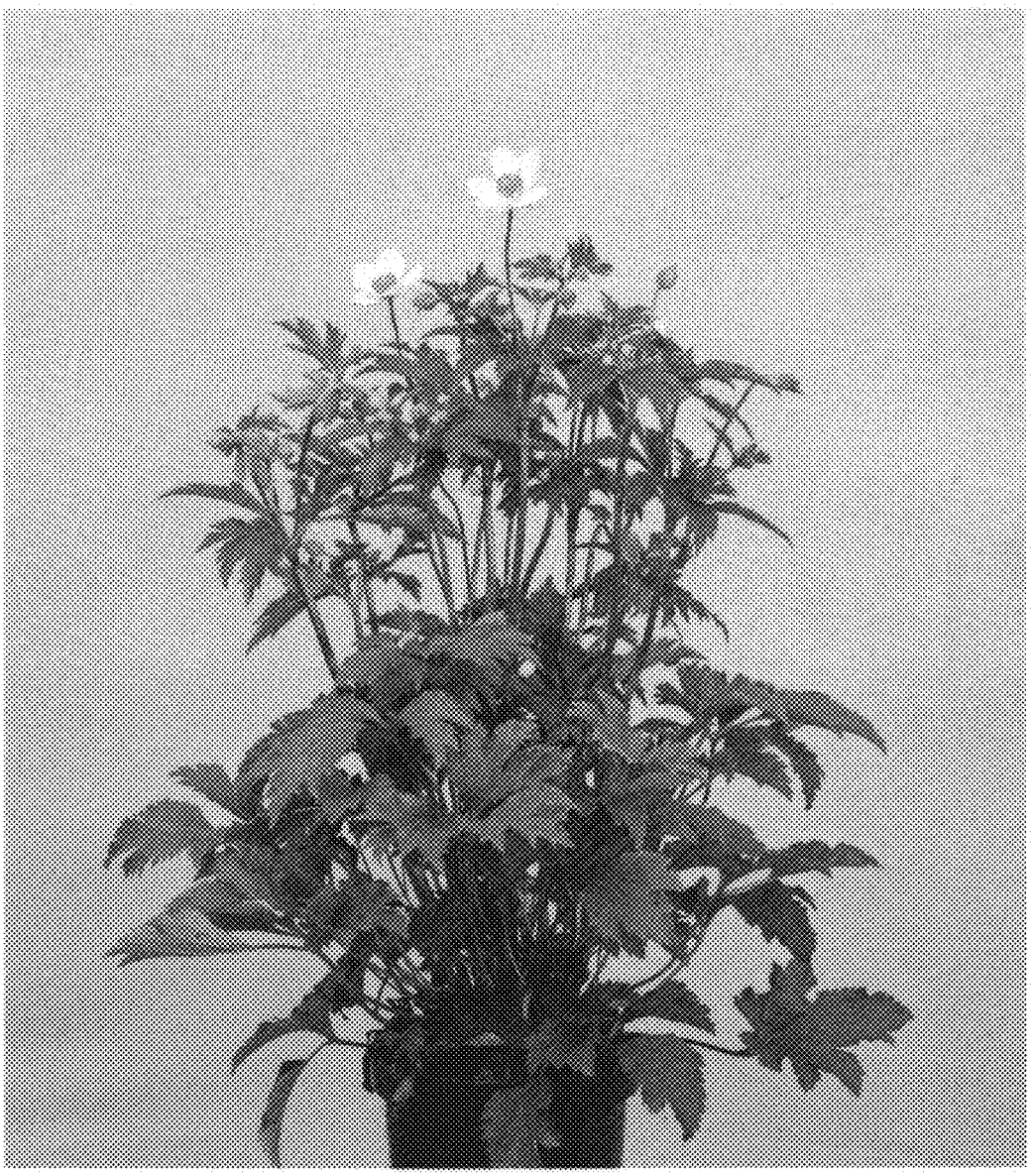
FIG. 1 shows, as nearly true as it is reasonably possible to make the same in color illustrations of this type, the typical foliage and growth characteristics of the new cultivar, 'Macane017'. The plant shown is approximately one year old, potted into a 17 cm nursery pot, grown outdoors in Kirkcudbright, Scotland at a commercial nursery.
Figure 2:
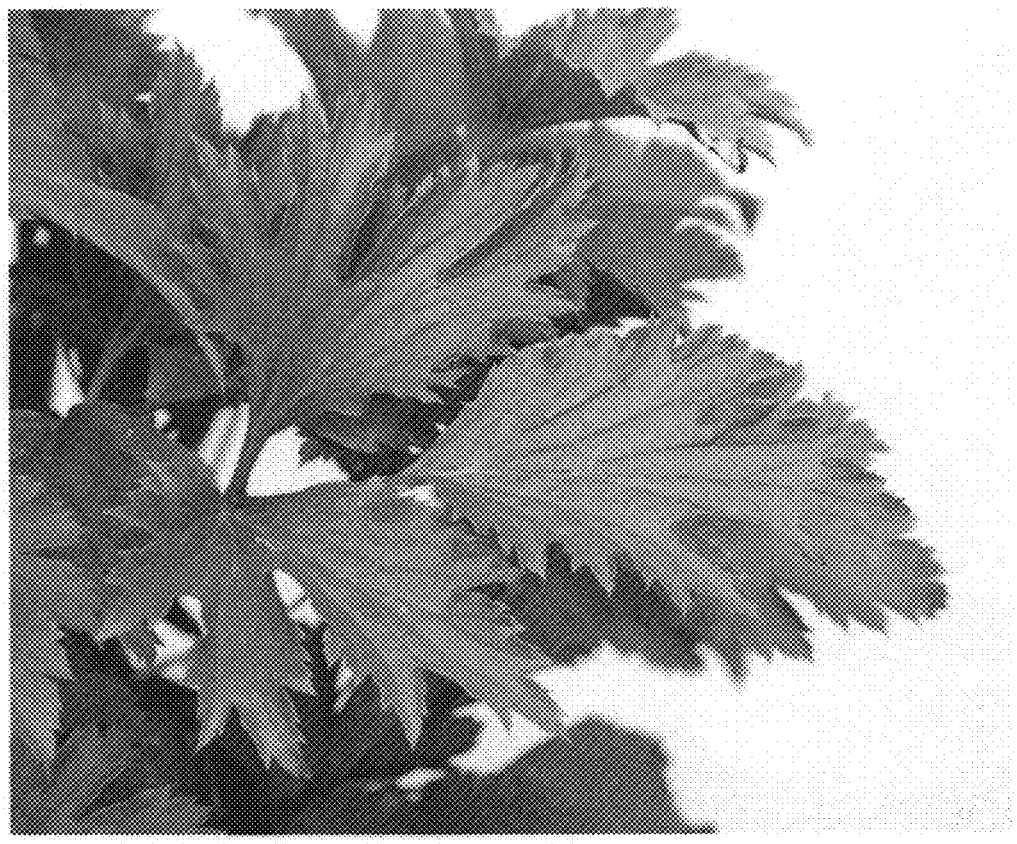
FIG. 2 shows, as nearly true as it is reasonably possible to make the same in color illustrations of this type, the typical foliage of the plant in FIG. 1.
Figure 3:
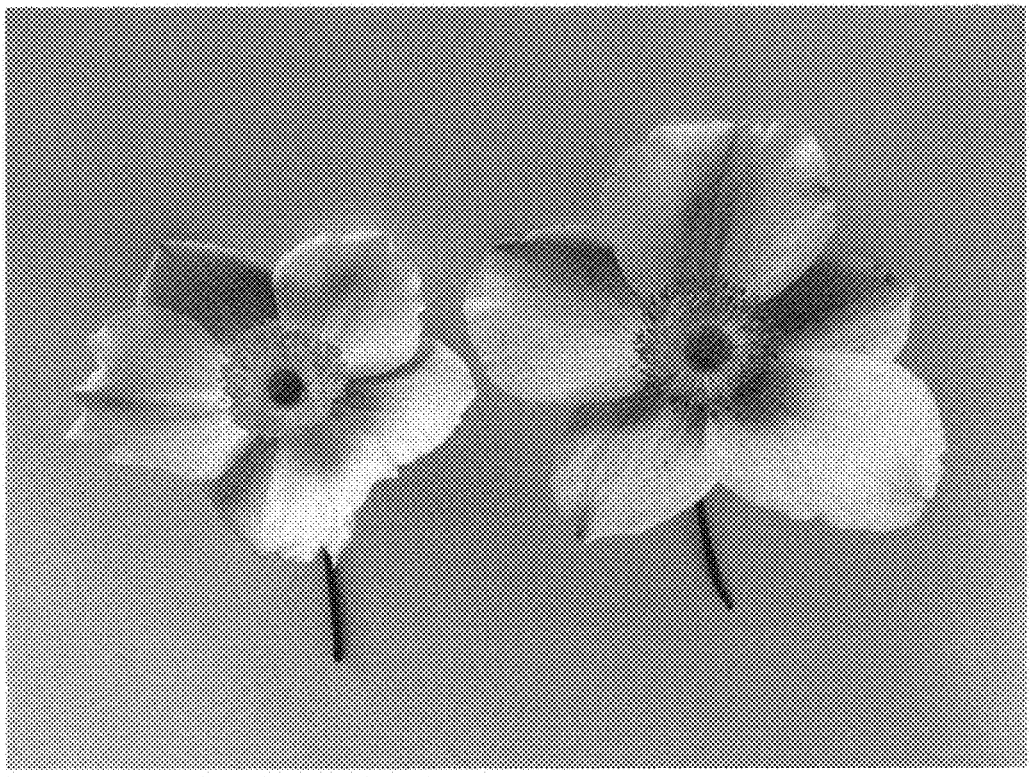
FIG. 3 shows, as nearly true as it is reasonably possible to make the same in color illustrations of this type, the typical flower of the plant in FIG. 1.
Figure 4:
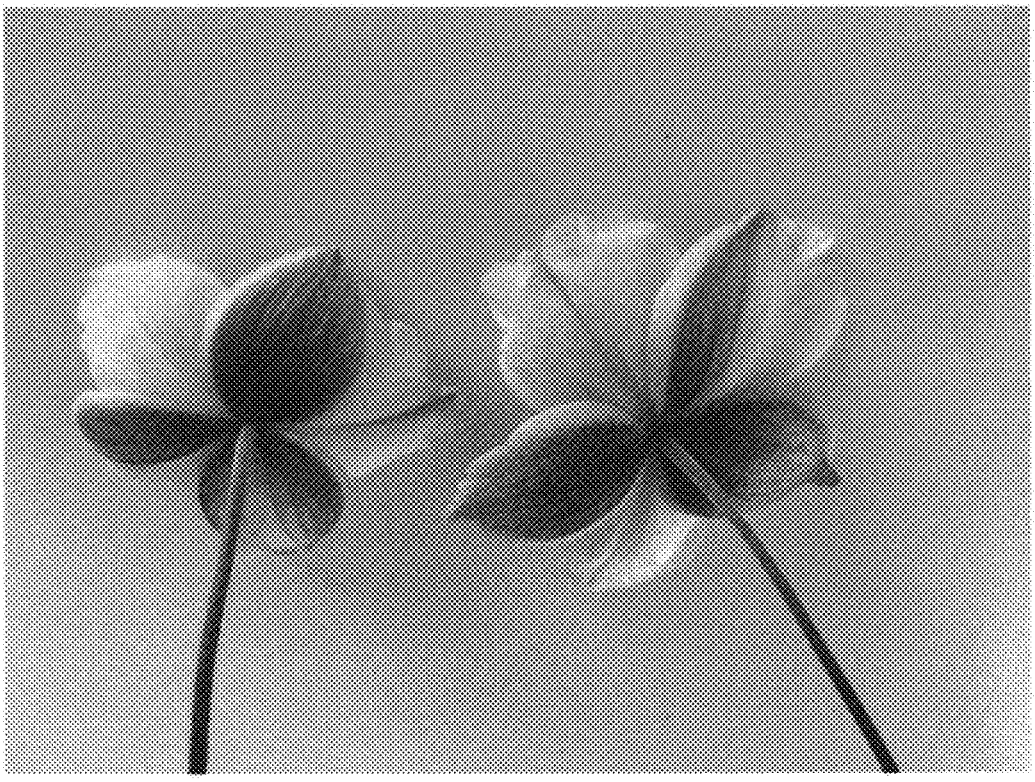
FIG. 4 shows, as nearly true as it is reasonably possible to make the same in color illustrations of this type, the lower surface of the 'Macane017' flower.

The following is a detailed botanical description of a new and distinct variety of *Anemone* hybrid known as 'Macane017', based upon observations of one year old plants, potted into 17 cm nursery pots and grown outdoors at a commercial nursery in Kirkcudbright, Scotland. Plants were grown in full sun to partial shade using accepted fertility and irrigation practices for *Anemone* plants. With the exception of nematicides, no chemical pest control measures were employed. Furthermore, no artificial light or photoperiodic treatments were given to the plants. Observation data was recorded in July of 2017.

Those skilled in the art will appreciate that certain characteristics will vary with older or, conversely, with younger plants. 'Macane017' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition, 2015.

A botanical description of 'Macane017' and comparisons with the parents and most similar variety of common knowledge are provided below.

General plant description:

*Growth habit.*—Herbaceous perennial; ovate plant form with leaves developing from basal rosettes; flowering stems arising from the rosette also bear foliage; no lateral branching is present.

*Growth rate.*—Moderate.

*Plant vigor.*—Moderate to high.

*Height.*—55.0 cm to the top of the foliar plane; 60.2 cm to the top of the floral plane.

*Width.*—56.5 cm.

*Propagation.*—Root cuttings and tissue culture.

*Time to produce flowering plant from rooted cutting.*—Approximately 6 to 8 weeks to produce a rooted young plant; 16 to 20 months to produce a marketable potted plant.

*Pest resistance and susceptibility.*—Plants have not been observed to be susceptible or resistant to pathogens and pests common to *Anemone* sp.

*Environmental tolerances.*—Adapt to, at least, USDA Zones 4 to 9 and temperatures ranging from minus 30 degrees Celsius to 35 degrees Celsius; moderate tolerance to rain; moderate tolerance to wind.

Root system:

*Type.*—Moderately fibrous root system.

*Branching.*—Very freely branched.

*Density.*—Moderately dense.

*Distribution.*—Roots distributed evenly throughout the soil profile, from shallow to deep.

*Diameter.*—Largest roots measuring 0.5 mm in diameter.

*Texture.*—Smooth; lacking root hairs.

*Color.*—Greyed-brown, nearest to in between RHS N199C and N199D.

Foliage:

*Arrangement.*—Leaves are borne both basally and on the flowering stems; on stems, arrangement is opposite.

*Attachment.*—Petiolate.

*Division.*—Trifoliate.

*Quantity.*—3 leaves per basal rosette; 3 leaves per flowering stem.

*Whole leaf shape.*—Basal leaves are broad ovate to near orbicular; leaves of flowering stems are broad ovate.

*Whole leaf dimensions.*—Basal leaves are 14.0 cm long, excluding the petiole, and 15.6 cm in width, on average. Leaves on flowering stems are 10.7 cm long and 11.4 cm wide.

*Leaflet shape.*—Basal leaves are ovate; leaves on flowering stems are narrow obovate.

*Leaflet dimensions.*—Basal leaves are 10.1 cm long and 6.3 cm wide. Leaves on flowering stems are 8.5 cm long and 4.0 cm wide.

*Leaf attitude.*—Basal leaves at an average angle of 60 degrees to the soil level; varying between 50 and 70 degrees. Leaves of the flowering stem are at an angle of approximately 45 degrees to the stem.

*Leaflet apex.*—All leaves are acute to finely apiculate.

*Leaflet base.*—All leaves are cuneate.

*Leaflet margin.*—All leaves are serrulate to incised.

*Lobes.*—All leaves with three lobes; sinus depth is medium to deep; sinus orientation is divergent.

*Texture, adaxial surface.*—All leaves are slightly rugose and glabrous.

*Texture, abaxial surface.*—All leaves are moderately rugose and glabrous.

*Luster, adaxial surface.*—Slightly glossy on all leaves.

*Luster, abaxial surface.*—Matte on all leaves.

*Color, all leaves.*—Juvenile foliage color, adaxial surface — Green, RHS 143A. Juvenile foliage color, abaxial surface — Green, RHS 138B. Mature leaf color, adaxial surface — Nearest to a mixture of green, RHS 137B, and yellow-green, RHS 146A. Mature leaf color, abaxial surface — Yellow-green, nearest to in between RHS 147C and 148B.

*Venation, all leaves.*—Type — Laciniate. Vein color, adaxial surface — Yellow-green, RHS 144B. Vein color, abaxial surface — Yellow-green, RHS 144A.

*Petiole.*—Dimensions — Petioles of the basal leaves are 16.4 cm long and 0.4 cm in diameter, on average. Petioles on flowering stems are 1.4 cm long and 0.4 cm in diameter. Apical leaflet petiole is 3.5 cm long and 0.3 cm in diameter and lateral leaflet petioles are 1.2 cm long and 0.3 cm in diameter. Strength — All petioles are strong. Color, adaxial surface — All petioles are yellow-green, nearest to RHS 144A. Color, abaxial surface — All petioles are yellow-green, nearest to RHS 144A. Texture, adaxial and abaxial surfaces — All petioles are moderately covered with short soft hairs; average length of hairs is 1.5 mm; colored white, nearest to RHS NN155D. Luster, adaxial and abaxial surfaces — All petioles are glossy.

*Stipules.*—General — Two leafy stipules present at the base of each leaf. Shape — Oblong to narrow ovate. Length — Average of 2.5 cm. Diameter — Average of 0.7 cm. Color, adaxial surface — Yellow-green, nearest to RHS 145B. Color, abaxial surface — Yellow-green, nearest to RHS 145B. Texture, adaxial surface — Smooth and glabrous. Texture, abaxial surface — Densely covered with short soft hairs; average length of hairs is 1.5 mm; colored white, nearest to RHS NN155D.

Inflorescence:

*Habit.*—Cyme.

*Natural flowering season.*—Summer through autumn in Kirkcudbright, Scotland.

*Time to flower or response time.*—Approximately 10 months.

*Height.*—54.9 cm.

*Diameter.*—14.3 cm.

*Quantity of flowers per inflorescence.*—1, on average.

*Quantity of flowers per plant.*—10, on average.

*Quantity of flower buds per plant.*—200, on average.

*Quantity of flowers and flower buds per plant.*—210, on average.

*Peduncles.*—Length — Average of 41.4 cm. Diameter — Average of 0.5 cm. Angle — Average angle to soil level is approximately 80 degrees. Strength — Strong. Texture — Smooth. Pubescence — Moderately covered with soft hairs; average length of hairs is 1.0 mm; hairs colored greyed-white, nearest to RHS 156D. Luster — Moderately glossy. Color — Yellow-green, nearest to a mixture of RHS 144A and 146A; moderately to heavily suffused with a combination of greyed-purple, nearest to RHS N186C, and brown, nearest to RHS 200B.

Bud:

*Shape.*—Ovate.

*Length.*—Average of 14 mm.

*Diameter.*—Average of 11 mm.

*Texture.*—Smooth.

*Pubescence.*—Dense wooly pubescence; average length of hairs is 1 mm; color of hairs is greyed-white, nearest to in between RHS 156C and 156D.

*Luster.*—Matte.

*Color.*—Brown, RHS N200B; underside is suffused with yellow-green, nearest to RHS N144D.

Flower:

*Type and form.*—Rotate; single.

*Aspect.*—Upright to slightly outward.

*Flowering habit.*—Freely flowering.

*Flower longevity on plant.*—Approximately 10 days.

*Persistent or self-cleaning.*—Self-cleaning.

*Fragrance.*—Non-fragrant.

*Diameter.*—Average of 6.2 cm.

*Depth.*—Average of 1.6 cm.

*Tepals.*—Quantity — Average of 6; varying between 5 and 7. Arrangement — Rotate; the unfused tepals arranged in 2 whorls. Length — 3.0 cm, on average; varying from 2.8 to 3.3 cm. Width — 2.4 cm, on average; varying from 2.1 to 2.7 cm. Shape — Obovate. Apex — Obtuse. Base — Cuneate. Margin — Entire; not undulated. Texture, luster and pubescence of the upper surface — Glabrous, slightly glossy, and moderately velvety. Texture, luster and pubescence of the lower surface — Smooth, slightly glossy, and densely covered with appressed soft, silky hairs; average length of hairs is 0.75 mm; colored greyed-white, RHS 156D. Color — When opening, upper surface — White, nearest to in between RHS NN155B and NN155C, and fading to green-white towards the base, nearest to in between RHS 157B and 157C. When opening, lower surface — White, nearest to RHS NN155A, and fading to green-white towards the base, nearest to RHS 157C. Lower tepals are partially or entirely colored purple, nearest to RHS N77D, and suffused with yellow-green towards the base, RHS 147A. Fully opened, upper surface — White, nearest to RHS NN155D, and fading to green-white towards the base, nearest to RHS 157D. Not fading. Fully opened, lower surface — White, nearest to in between RHS NN155C and NN155D, and fading to green-white towards the base, nearest to RHS 157D. Lower tepals are partially or entirely colored purple, nearest to RHS N79D, and suffused with yellow-green towards the base, nearest to RHS 147A. Not fading. Tepal venation — Fully opened, upper surface — White, RHS NN155D, and fading to green-white towards the base, nearest to RHS 157D. Fully opened, lower surface — White, nearest to in between RHS NN155C and NN155D, and fading to green-white towards the base, nearest to RHS 157D. Lower tepals are partially or entirely colored purple, nearest to RHS N79D, and suffused with yellow-green towards the base, nearest to RHS 147A.

*Pedicels.*—Length — Average of 8.8 cm. Diameter — Average of 0.2 cm. Angle — Primary flowers at an angle of 0 degrees to peduncle axis; lateral flowers are at an average angle of 30 degrees to the peduncle axis. Strength — Moderately strong. Texture — Smooth. Pubescence — Densely covered with short soft hairs; average length of hairs is 0.75 mm; colored greyed-white, nearest to in between RHS 156C and 156D. Luster — Slightly glossy. Color — Yellow-green, nearest to RHS 148A; heavily suffused with brown, nearest to RHS 200A, where exposed to sunlight.

Reproductive organs:

*Stamens.*—Quantity — Approximately 230. Anthers — Shape — Oblong. Length — Approximately 1.5 mm. Width — Approximately 0.75 mm. Color — Yellow-orange, RHS 17B. Filaments — Length — 8 mm, on average. Color — Yellow-green, nearest to RHS 150D. Pollen — Color — Yellow, RHS 11D. Quantity — Low.

*Pistil.*—Quantity — 175, on average. Length — 1.0 mm. Style — Length — 0.5 mm. Color — Green, RHS 143C. Stigma — Shape — Club-shaped. Dimensions — 0.5 mm long and 0.5 cm in diameter. Color — Yellow-green, nearest to RHS N144D. Ovary Color — Yellow-green, RHS 144A.

Seed and fruit: No fruit or seeds have been detected to date.

COMPARISONS WITH THE PARENT PLANTS

Plants of the new cultivar 'Macane017' may be distinguished from its seed parent, an unnamed *Anemone rupicola* x *Anemone hupehensis* var. japonica 'Pamina' F1 hybrid seedling, by the characteristics described in Table 1.

TABLE 1

| Characteristic | 'Macane017' | Unnamed seed parent |
|---|---|---|
| Mature plant height. | 50 to 60 cm. | 70 to 80 cm. |
| Flowering season. | Summer through autumn in Kirkcudbright, Scotland. | Early to late summer in Kirkcudbright, Scotland. |
| Flower diameter. | 6.2 cm. | 8.0 cm. |

Plants of the new cultivar 'Macane017' differ from the pollen parent, an unnamed *Anemone hupehensis* seedling with a dwarf growth habit and a pink double flower, by the characteristics described in Table 2.

TABLE 2

| Characteristic | 'Macane017' | Unnamed pollen parent. |
|---|---|---|
| Plant height | 50 to 60 cm. | 30 cm. |
| Flowering season. | Summer through autumn in Kirkcudbright, Scotland. | September in Kirkcudbright, Scotland. |
| Flower habit; petal count | Single. | Semi-double. |
| Flower color. | White with dark violet-blue reverse. | Mid pink. |

COMPARISONS WITH THE MOST SIMILAR VARIETY OF COMMON KNOWLEDGE

Plants of the new cultivar 'Macane017' are most similar to the commercial variety, *Anemone* 'MACANE001' (U.S. Plant Pat. No. 23,132). A comparison of 'Macane017' with *Anemone* 'MACANE001' is described in Table 3.

TABLE 3

| Characteristic | 'Macane017' | 'Mancane001' |
|---|---|---|
| Growth habit. | More freely branching and more compact. | Less freely branched and less compact. |
| Flowering season. | Flowers later. | Flowers earlier. |
| Flower diameter. | 6.2 cm. | 9.0 cm. |

That which is claimed is:

1. A new and distinct variety of *Anemone* plant named 'Macane017', substantially as described and illustrated herein.

* * * * *